(12) United States Patent
Gomez-Llorens

(10) Patent No.: US 8,348,826 B2
(45) Date of Patent: Jan. 8, 2013

(54) SURGICAL IMPLANT, IN PARTICULAR ARTIFICIAL SPHINCTER WITH ADJUSTED PRESSURE

(75) Inventor: Christophe Gomez-Llorens, Reims (FR)

(73) Assignee: Zephyr Surgical Implants, Villeurbanne (FR)

( * ) Notice: Subject to any disclaimer, the term of this patent is extended or adjusted under 35 U.S.C. 154(b) by 287 days.

(21) Appl. No.: 12/680,587

(22) PCT Filed: Oct. 24, 2008

(86) PCT No.: PCT/FR2008/051927
§ 371 (c)(1),
(2), (4) Date: Apr. 12, 2010

(87) PCT Pub. No.: WO2009/056750
PCT Pub. Date: May 7, 2009

(65) Prior Publication Data
US 2010/0211175 A1  Aug. 19, 2010

(30) Foreign Application Priority Data
Oct. 24, 2007  (FR) ..................................... 07 58552

(51) Int. Cl.
*A61F 2/02* (2006.01)
*A61B 17/12* (2006.01)
(52) U.S. Cl. .......................................... 600/31; 606/157
(58) Field of Classification Search .............. 600/29–31, 600/37; 606/151, 157; 417/258
See application file for complete search history.

(56) References Cited

U.S. PATENT DOCUMENTS

| | | | |
|---|---|---|---|
| 4,167,952 A | 9/1979 | Reinicke | |
| 4,197,835 A | 4/1980 | Reinicke | |
| 4,256,093 A * | 3/1981 | Helms et al. | 600/31 |
| 4,682,583 A * | 7/1987 | Burton et al. | 600/31 |
| 4,878,889 A * | 11/1989 | Polyak | 600/31 |
| 4,917,110 A * | 4/1990 | Trick | 600/40 |
| 4,958,630 A * | 9/1990 | Rosenbluth et al. | 600/40 |
| 4,982,731 A * | 1/1991 | Lue et al. | 600/40 |
| 4,994,020 A | 2/1991 | Polyak | |
| 5,048,511 A * | 9/1991 | Rosenbluth et al. | 600/40 |
| 7,011,622 B2 * | 3/2006 | Kuyava et al. | 600/31 |
| 7,273,448 B2 * | 9/2007 | Arnal et al. | 600/30 |
| 7,874,978 B2 * | 1/2011 | Kuyava et al. | 600/40 |
| 2002/0022759 A1 | 2/2002 | Forsell | |

* cited by examiner

*Primary Examiner* — Julian Woo
*Assistant Examiner* — Christopher L Templeton
(74) *Attorney, Agent, or Firm* — Dennison, Schultz & MacDonald

(57) ABSTRACT

A surgical implant includes an inflatable element that is inflatable responsive to fluid pressure; a tank for fluid under pressure in communication with the inflatable element to regulate the pressure of the element; a manually controlled pump in communication firstly with the inflatable element via a one-way check valve, and secondly with the tank via a one-way check valve; and a control unit incorporating the tank and the manual pump. The control unit presents a through opening for the fluid, the opening being in communication firstly on the inside of the control unit with the tank and the manual pump, and secondly on the outside of the control unit solely with the inflatable elements via a catheter mounted between the inflatable element and the control unit. The tank is formed by a leaktight chamber of fluid under pressure defined by a movable piston elastically biased by a spring.

11 Claims, 2 Drawing Sheets

SURGICAL IMPLANT, IN PARTICULAR ARTIFICIAL SPHINCTER WITH ADJUSTED PRESSURE

The present invention relates to the technical field of surgical implants suitable for controlling the inflation of an element that is inflatable in response to fluid pressure.

A particularly advantageous application of the invention lies in constituting artificial urinary sphincter for man or woman, an artificial anal sphincter, an artificial pylorus or esophagus sphincter, or to constitute a gastric band.

In the preferred application of an artificial urinary sphincter, various systems are known for providing a solution to urinary incontinence, in particular in man. For example, U.S. Pat. No. 4,222,377 describes an artificial urinary sphincter comprising, as its inflatable element, an occluding cuff for implanting around a segment of the urethral duct. The cuff is constituted by a flexible and inextensible reinforced outer portion having bonded thereto an inner cushion that is inflatable by a fluid under pressure.

The artificial urinary sphincter also includes a pressure-regulator balloon for implanting in the space close to the bladder, enabling the occluding cuff, when in the closed position, to exert on the urethral segment pressures that are close to physiological values. This compression of the tissue of the urethra needs to prevent urine from passing while allowing a flow of blood to pass, thereby limiting any risk of tissue hypoxia and necrosis.

The artificial urinary sphincter also includes a pump in the scrotum (skin covering the testicles) of a man or in one of the labia majora of a woman. In its bottom portion, the pump has a bulb that the patient compresses to open the artificial sphincter at the time of miction. The pump has two circuits in parallel. Thus, the pump is fitted with a first catheter connecting the pump to the bulb via a non-return system having balls mounted on a spring. The pump also has a second catheter mounted between the pump and the inflatable cuff, via a non-return system using balls. Furthermore, the cuff is connected to the bulb via a calibrated orifice.

In order to ensure continence of the patient, the fluid flows freely between the cuff and the balloon that maintains a determined pressure in the cuff. This pressure that is applied by the cuff on the urethra is sufficient to ensure continence, but remains too small to stop arterial and venous blood flow. The compressed tissues therefore remain irrigated, thus reducing the risk of ischemia.

To enable the patient to urinate, the fluid contained in the cuff needs to be emptied into the balloon so as to stop compressing the urethra. To do this, the patient actuates the bulb of the pump situated in the scrotum, so that under the action of pressure on the bulb, the duct communicating with the cuff is closed by the ball check valve, and the liquid from the bulb pushes back the ball check valve that was closing the duct communicating with the balloon, thereby enabling the balloon to be filled. When the bulb applies suction, the duct communicating with the cuff is released by the ball being sucked back, thereby causing the cuff to empty into the bulb. The duct communicating with the balloon is closed under the action of the spring. Pressure is applied repeatedly to the bulb until the cuff has been emptied. The patient knows that the cuff is empty when the bulb of the pump is flat, thus enabling the patient to urinate. Simultaneously, the balloon fills the cuff from the bulb via the calibrated orifice. Filling takes place slowly (over about 180 seconds), thereby allowing the patient to empty the bladder completely before the cuff compresses the urethra once more.

That artificial urinary implant raises various drawbacks.

Implanting such an artificial urinary implant requires three surgical actions to be performed:
 a perineal incision for placing the cuff around the urethra;
 an inguinal incision for penetrating into the pelvis and placing the pressure-regulator balloon between the bladder and the iliac vessels;
 providing a space in the scrotum for receiving the pump.

The risks for the patient are as follows:
 the inguinal incision may give rise to a nosocomial infection that will require the implant to be removed;
 the position of the pressure-regulator balloon in contact with the iliac vein can give rise to phlebitis and thus to a pulmonary embolism;
 the anticoagulation treatment that is prescribed for the seven postoperative days in order to prevent phlebitis that might lead to thrombocytopenia; and
 a hospital stay with a duration of 4 to 5 days.

Furthermore, the pressure-regulator balloon is made of a material that is elastic, but porous, which leads to an irremediable loss of the filler liquid, thus not making it possible to ensure a selected determined pressure for the cuff.

In practice, the artificial urinary sphincter as described above is delivered in the form of a kit that needs to be prepared by the surgical team at the time of implantation.

The kit includes in particular a plurality of balloons for different pressures, a control pump, a plurality of cuffs of different sizes for fitting to each type of urethra, and a connection unit.

Before being implanted in the organism, it is appropriate to measure the urethra and to select a size for the cuff, and also to select a balloon presenting a pressure from amongst those available. The cuff, the pressure balloon, and the control pump need to be filled with a specific mixture of sterile water and contrast liquid. The mixture needs to be prepared by the surgeon for each operation. Each element then needs to be debubbled. Furthermore, two clips need to be sheathed by the surgeon and then placed on each of the catheters in order to seal off each portion making up the kit. That design requires the surgeon to be assisted by a nurse on each occasion an artificial urinary sphincter is implanted. To summarize, implanting an artificial urinary sphincter is an operation that is risky for the patient, relatively complex and lengthy, and consequently expensive.

U.S. Pat. No. 4,994,020, which uses the same operating principle as U.S. Pat. No. 4,222,377, describes a surgical implant including an inflatable element that is inflatable in response to fluid pressure, a tank for the fluid under pressure in communication with the inflatable element to regulate the pressure of said element, a manually controlled pump in communication firstly with the inflatable element via a one-way check valve, and secondly with the tank via a one-way check valve. It should be observed that an additional tank is provided to participate in regulating pressure. That surgical implant also includes a control unit incorporating the tank and the manual pump. The control unit has a through opening for passing the fluid that is in communication firstly inside the control unit with the tank and the manual pump, and secondly outside the control unit with the inflatable element, via a catheter that is mounted between the inflatable element and the control unit.

The tank includes an extensible thin membrane that expands under pressure from the fluid. The extensible thin membrane is typically made of silicone, a material of porosity that is not zero and that increases over time. As a result, the patient's body has transferred thereto the hydraulic fluid and microparticles, or indeed bacteria accidentally inoculated when filling the implant. Furthermore, that transfer of hydraulic fluid gives rise, in the long term, to a reduction of the pressure in the cuff, thereby leading to the patient suffering from leaks of urine.

Given the design of that implant, it is also found in practice that it is necessary to include an additional tank so as to provide pressure regulation that is sufficient over time. The additional tank is made using an extensible membrane and it presents the same drawbacks as the main tank, while making the implant bulky for implanting in the scrotum.

The present invention seeks to remedy the drawbacks of the state of the art by proposing a novel surgical implant designed to limit the risks associated with putting such a surgical implant into place, while being adapted to provide regulation that is accurate, stable, and constant over time for the pressure of an inflatable element.

Another object of the invention is to provide a novel surgical implant that minimizes or even eliminates losses of regulation fluid.

Another object of the invention is to provide a novel surgical implant that is practically ready for use prior to each implantation.

Another object of the invention is to provide a novel surgical implant designed to present operation that is safe and reliable, and in particular a regulated pressure that is stable over time.

To achieve these objects, the invention provides a surgical implant comprising:

an inflatable element that is inflatable in response to fluid pressure;
a tank for fluid under pressure in communication with the inflatable element to regulate the pressure of said element;
a manually controlled pump in communication firstly with the inflatable element via a one-way check valve, and secondly with the tank via a one-way check valve; and
a control unit incorporating the tank and the manual pump, the control unit presenting a through opening for the fluid, the opening being in communication firstly on the inside of the control unit with the tank and the manual pump, and secondly on the outside of the control unit solely with the inflatable element via a catheter mounted between the inflatable element and the control unit.

According to the invention, the tank is formed by a leaktight chamber of fluid under pressure defined by a movable piston elastically biased by a spring.

According to a preferred embodiment characteristic, the tank is formed by a leaktight chamber of fluid under pressure that is defined by elastically-biased movable piston.

For example, the tank comprises a cylinder having a sealing membrane mounted therein that is fastened between the piston and the cylinder.

In a preferred embodiment, the piston is elastically-biased by a spring mounted inside the cylinder and bearing against a mounting support.

It should be observed that the spring is immersed in a confined fluid medium that is different from the fluid under pressure and that forms a compensation volume for compensation relative to the volume of the chamber.

For example, the piston on its side opposite from the chamber defines a compensation volume that is closed by a deformable wall confining the fluid medium in which the spring is immersed.

According to another characteristic of the subject matter of the invention, the cylinder is closed opposite from the piston by an end wall defining:

a circuit providing communication between the chamber and the though opening;
a circuit providing communication between the chamber and the pump; and
a circuit providing communication between the pump and the through opening.

Advantageously, the pump includes a movable actuation wall mounted on the cylinder and internally defining a variable-volume supply of fluid that is in communication with the circuits providing communication between the pump and the through opening, and between the pump and the chamber of the tank.

For reasons of compactness, the wall of the pump extends over substantially the entire height of the cylinder, being provided with ridges ($35_1$) to assist in actuating it.

According to another characteristic of the invention:

the circuit providing communication between the chamber and the through opening is provided with a calibrated leak orifice to regulate the pressure of the inflatable element; and
the circuit providing communication between the pump and the chamber is provided with the one-way check valve that is elastically biased towards its closed, rest position.

In order to enable the implant to be activated and deactivated, the control unit includes a control switch for closing the circuit providing communication between the tank and the inflatable element.

Preferably, the control switch is accessible from either side of the control unit.

In an exemplary application to an artificial urinary sphincter, the inflatable element is in the form of a cuff suitable for surrounding an organ having an internal passage so as to be closed or opened by constriction applied by said inflatable element.

Various other characteristics appear from the following description given with reference to the accompanying drawings which show, as non-limiting examples, embodiments of the subject matter of the invention.

Figure 1:
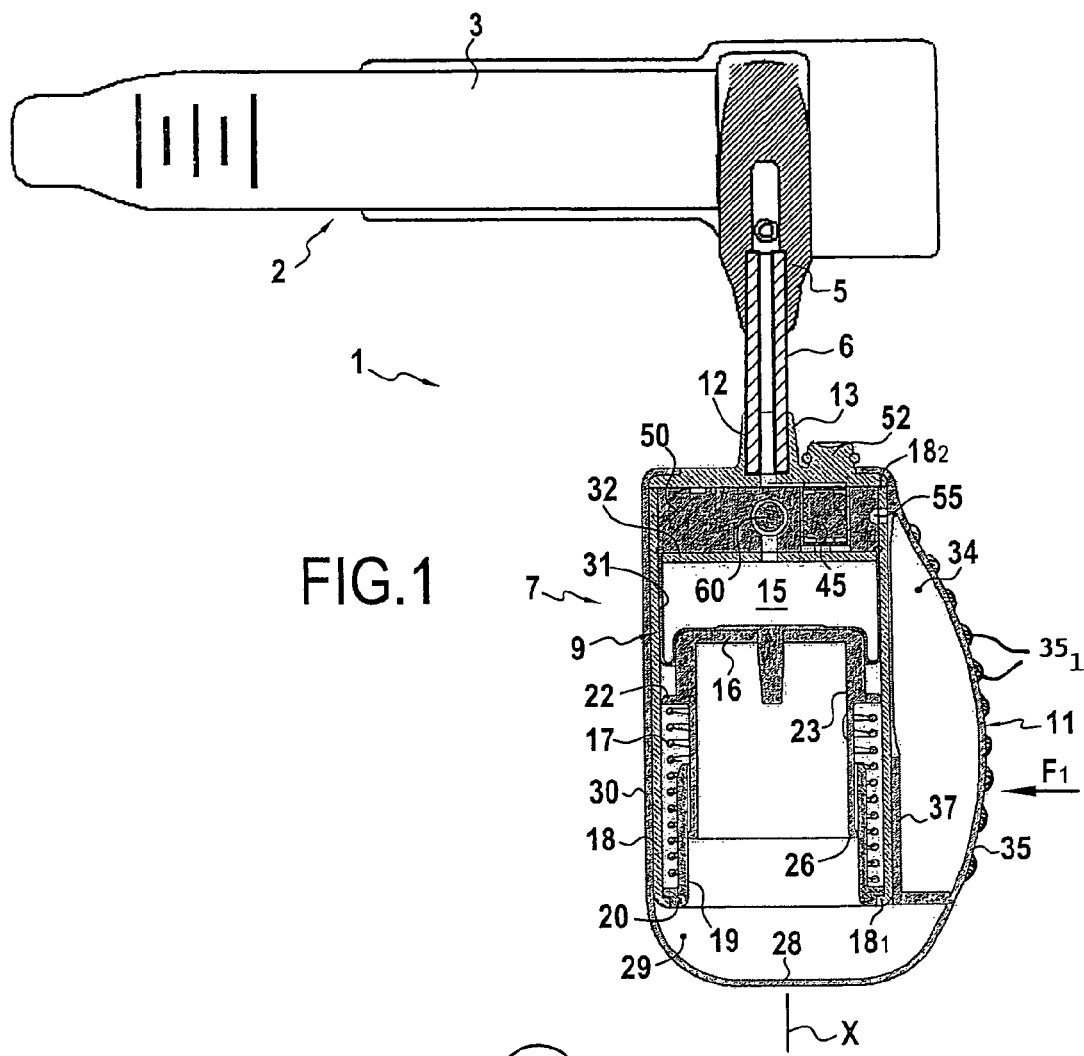
FIG. 1 is an elevation section view showing an embodiment of a surgical implant in accordance with the invention.

As can be seen more precisely from the figures, the subject matter of the invention relates to a surgical implant 1 including an inflatable element 2 that is inflatable in response to fluid pressure. In the embodiment shown, the inflatable element 2 is in the form of a cuff 3 suitable for surrounding an organ having an internal passage that is to be closed or opened by being constricted by said inflatable element 2. In this application, the surgical implant is suitable for forming an artificial sphincter, in particular a urinary sphincter.

In this embodiment, the cuff 3 comprises an inextensible flexible strip having an inflatable cushion bonded thereto that is inflatable by a fluid under pressure. The cuff 3 is suitable for being folded in half and retained in its closed position so as to surround an organ having an internal passage that is to be closed or opened at will.

The inflatable element 2 includes a socket 5 enabling the inflatable cushion 4 to be connected to a catheter or duct 6 for connection to a control unit 7.

According to an advantageous characteristic of the invention, the control unit 7 incorporates a tank 9 for the fluid under pressure and a pump 11 that is controlled manually in order to cause the fluid to flow, as described below in the description. The control unit 7 has a through opening 12 for the fluid, which opening is connected to the catheter 6. For this purpose, the control unit 7 has a socket 13 for connection with the catheter 6, and defining internally the through opening 12. As can be seen more clearly in FIG. 1, the through opening 12 is in communication firstly on the outside of the control unit 7 solely with the inflatable element 2 via the catheter 6, and secondly, on the inside of the control unit 7, with the tank 9 and the manual pump 11 via fluid flow circuits that are described in greater detail in the description below.

According to a preferred embodiment characteristic, the tank 9 is formed by a leaktight chamber 15 containing the fluid under pressure, and presenting a volume that is variable under the action of an elastically-biased movable piston 16. The movable piston 16 is biased elastically by a spring 17, e.g. a coil spring. In the example shown, the tank 7 comprises a cylinder 18 having a stationary or rigid wall, e.g. of circular right cross-section presenting a longitudinal axis of symmetry X.

The movable piston 16 is slidably mounted inside the cylinder 18, being biased by the spring 17 that is mounted to bear against a support 19 fastened to the cylinder 18.

In the example shown, the support 19 is in the form of a ring that is provided at its base with a projecting rim 20 that is fastened to one end of the cylinder 18, e.g. an end $18_1$. The support 19 thus extends inside the cylinder 18 over a fraction of its length, co-operating therewith to define a housing for the spring 17. The spring 17 thus bears between the projecting rim 20 and a projecting collar 22 that extends outside a skirt 23 projecting at right angles from the wall of the piston 16. The skirt 23 is mounted to extend inside the support 19 for the purpose of guiding the piston 16 by means of a shouldered rim 26 carried by the free end of the skirt 23. The spring 17 is calibrated to keep the fluid at a determined pressure that is preferably greater than the pressure that exists in the internal passage but less than blood pressure so as to close the internal passage of the organ while allowing blood to circulate. Typically, the spring 17 is calibrated to maintain the fluid at a determined pressure lying in the range 61 millibars (mbar) to 70 mbar.

Figure 7:
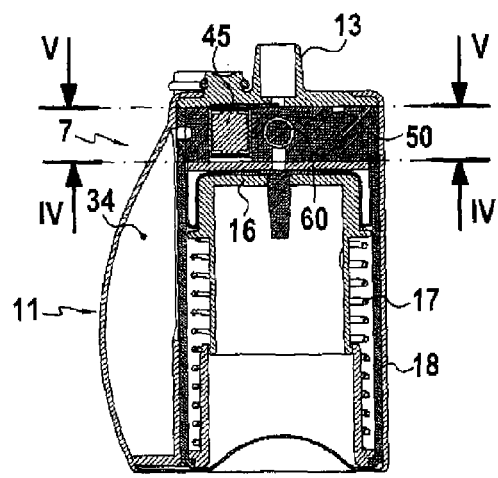
FIG. 7 is an elevation section view of the surgical implant showing the tank empty.

According to a preferred embodiment characteristic, the spring 17 is immersed in a fluid medium such as physiological serum, for example. This fluid medium is different from the fluid under pressure contained in the tank 9 and is confined by an outer membrane or skin 28 that thus closes the end $18_1$ of the cylinder. This fluid medium serves to form a compensation volume 29 relative to the volume of the chamber 15. As can be seen from the description below, this outer membrane 28 is designed to move between a concave extreme position (FIG. 7 showing the chamber 15 empty) and a convex extreme position (FIG. 1) as a function of the position of the piston 16. Preferably, this outer membrane 28 extends a tubular sleeve 30 surrounding the cylinder 18. The tubular sleeve 30 is closed at one end by the outer membrane 28.

As can be seen more precisely in FIGS. 1 and 7, the piston 16 is mounted in leaktight manner inside the cylinder, preferably with the help of an inner membrane or tubular skin 31 fastened between the piston 16 and the cylinder 18. This inner membrane 31 is fastened to the piston 16 by being pressed into the inside wall of the cylinder 19 to an end wall 32 closing the cylinder 18. By way of example, one of the ends of the inner membrane 31 is fastened to the piston 16, while its other end is wedged between the end wall 32 and the cylinder 18.

This inner membrane 31 thus rolls between the piston 16 and the cylinder 18. It should be observed that the piston 16 presents a diameter that is smaller than the diameter of the cylinder 18 so that the periphery of the piston 16 co-operates with the cylinder 18 to define a housing for the inner membrane 31. The chamber 15 of the tank 9 is thus defined inside the rigid cylinder 18 between the movable piston 16 and the closure end wall 32 of the cylinder, or given the way the inner membrane 31 is mounted, by the internal volume defined by said inner membrane 31 in co-operation with the closure end wall 32.

According to an advantageous embodiment characteristic, the manual pump 11 forms a chamber 34 for confining the fluid under pressure, and accessible from the outside of the control unit 7.

Figure 4:
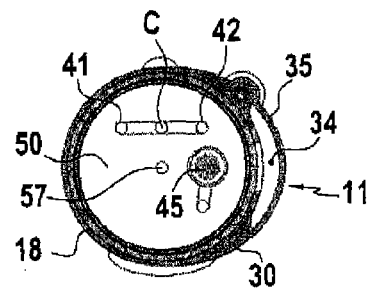
FIGS. 4 and 5 are cross-section views taken substantially on lines IV and V respectively in FIG. 7.
Figure 5:
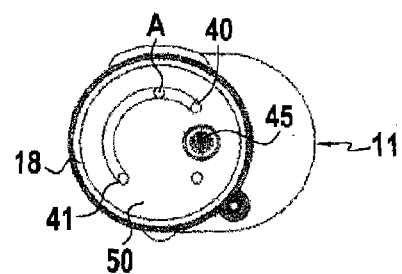
Figure 6:
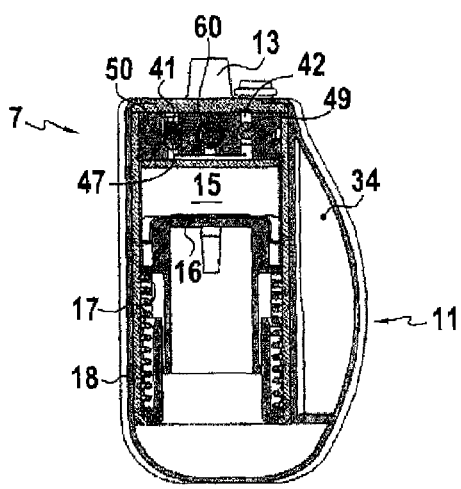
FIG. 6 is an elevation view on another section plane showing the surgical implant in accordance with the invention.

Advantageously, the manual pump 11 has a movable actuation wall 35 mounted outside the cylinder 18 over a limited angular range, e.g. less than 180°, as can be seen clearly in FIGS. 4 and 5. The actuation wall 35 extends at a distance from the cylinder 18 so as to define the variable volume supply 34 of fluid under pressure. The actuation wall 35 is provided externally with projections or ridges making it easier for the patient to locate. The pump 11 is thus actuated by pressing on the deformable wall 35 in the direction of arrow $F_1$ (FIG. 1) such that the action on the pump control is applied substantially perpendicularly to the longitudinal axis X of the control unit 7.

Advantageously, the deformable wall 35 extends at a distance from a portion of the sleeve 30 surrounding the cylinder 18. In other words, the supply of fluid 34 of said manual pump forms a projection on one side of the cylinder 18, e.g. along its entire height. Preferably, the sleeve 30, the actuation wall 35, and the outer membrane 28 form a single piece that is mounted on the cylinder 18 and that is made as a piece of molded silicone, for example. Naturally, the supply of fluid under pressure 34 is isolated from the fluid medium of the compensation volume 29.

The control unit 7 advantageously comprises:

- a circuit 40 providing communication between the chamber 15 of the tank 9 and the through opening 12;
- a circuit 41 providing communication between the chamber 15 of the tank 9 and the pump 11, and more particularly the supply of fluid 34; and
- a circuit 42 providing communication between the pump 11, and more precisely the supply of fluid 34, and the through opening 12.

It should be understood that the surgical implant 1 thus presents a closed circuit for circulating a fluid under pressure, which closed circuit is made up of the inflatable cushion 4, the catheter 6, the chamber 15 of the tank 9, the supply of fluid 34 of the pump 11, and the communication circuits 40 to 42 that are described in greater detail below. By way of example, the fluid under pressure that circulates in such a circuit may be physiological serum.

Figure 2:
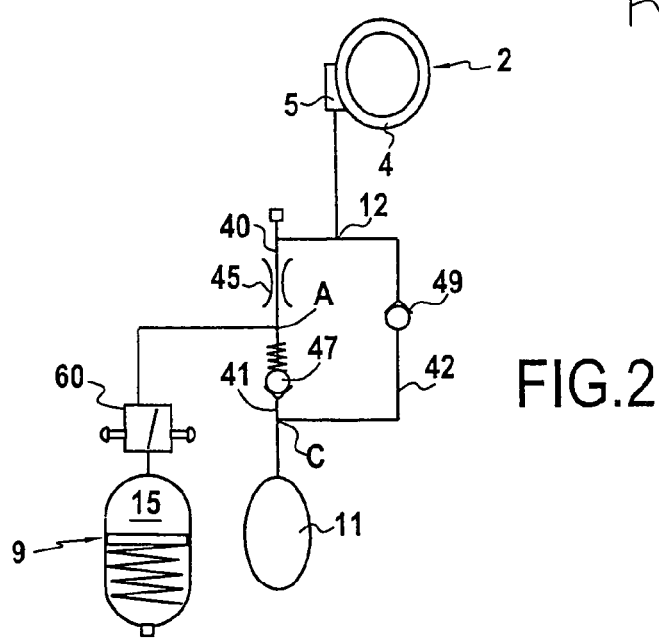
FIG. 2 is a diagram showing the operating principle of the surgical implant in accordance with the invention.

As can be seen more precisely in FIG. 2, the circuit 40 providing communication between the chamber 15 and the through opening 12 is provided with a calibrated leak orifice 45 adapted to regulate the pressure of the inflatable element 2 as explained below. The circuit 41 providing communication between the supply of fluid 34 of the pump 11 and the chamber 15 is provided with a one-way check valve 47 that is elastically biased towards its closed, rest position. For example, the one-way check valve 47 comprises a valve member pressed against its seat by means of a spring. The check valve 47 is closed when the pressure beside the pump 11 (point C) is less than the pressure at the point A situated beside the chamber 15. In contrast, the one-way check valve 47 is in the open position when the pressure at point C is greater than the pressure at point A.

The circuit 42 providing communication between the supply of fluid 34 of the pump 11 and the through opening includes a one-way check valve 49 such as a drain valve as explained in the description below. The drain valve 49 is in the closed position when the pressure at point C is greater than the pressure in the through opening 12. Conversely, the valve 49 is in the open position when the pressure in the through opening 12 is greater than the pressure at point C.

According to another advantageous characteristic of the subject matter of the invention, the communication circuits 40, 41, and 42 are arranged in a distribution block 50 associated with the end of the cylinder 18. More precisely, the distribution block 50 is mounted between the end wall 32 directly defining the chamber 15 and a cover 52 that closes the end $18_2$ opposite from the end $18_1$ of the cylinder. The cover 52 is advantageously provided with the connection socket 13 that defines the through opening 12. The tubular sleeve 30 is preferably fastened via its free edge to the cover 52.

Figure 3:
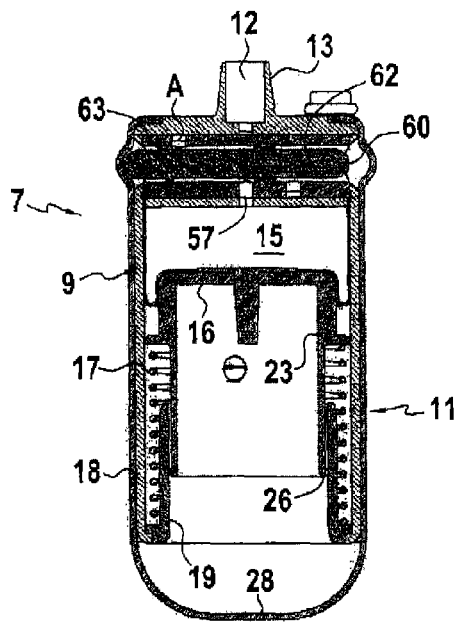
FIG. 3 is an elevation section view of a surgical implant in a position characteristic of activation.

The distribution block 50 includes ducts or channels that are arranged to provide the above-described circuits 40 to 42. The distribution block 50 also incorporates the check valves 45, 47, and 49. As can be seen more clearly in FIG. 1, a hole 55 is formed in the wall of the cylinder 18 so as to provide communication at the point C between the supply 34 of the manual pump 11 and the circuits 41 and 42 (FIG. 4). Similarly, the end wall 32 is provided with a through hole 57 opening out into the distribution block 50 so that the chamber 15 of the tank is connected to point A where the circuits 40 and 41 communicate with each other (FIGS. 3 and 5).

According to an advantageous embodiment characteristic, a switch 60 is provided that enables the tank 9 to be isolated from the inflatable element 2 so as to place the control unit 7 in a deactivated state. As can be seen more clearly in FIG. 3, the switch 60 is in the form of a control pin placed inside a bore 62 suitable for providing communication between the outlet hole 57 from the chamber 15 and the point A, i.e. specifically the point where the communication circuit 40 is connected to the through opening 12 via the calibrated orifice 45. The bore 62 is arranged in the distribution block 50 in a direction perpendicular to the axis X, and preferably also perpendicular to the direction $F_1$ that thrust is applied to the tank 11 (FIG. 1). The bore 62 preferably opens out to opposite sides of the distribution block 50 so that the pin 60 can be accessible from opposite sides of the control unit 7 through the sleeve 30. The pin 60 is provided with gaskets 63 adapted so that in the activated and deactivated positions, the pin 60 occupies positions that ensure respectively communication and no communication between the chamber 15 and the point A, and consequently, the inflatable element 2. Moving the pin 60 in one direction enables the control unit 7 to be put into its deactivated position (closure between the point A and the outlet hole 57), while moving it in the opposite direction enables the control unit 7 to be placed in its activated position (communication between the point A and the outlet hole 57, FIG. 3). Naturally, the pin 60 co-operates with abutments so that it occupies activated and deactivated positions that are stable.

The operation of the surgical implant 1 stems directly from the above description.

The description below applies to an artificial urinary sphincter. Under such circumstances, the inflatable cuff is implanted around a segment of the urethral duct, while the control unit 7 is implanted in the scrotum.

The patient should be considered as being continent when the cuff 3 is inflated and occlusive. In this position, the fluid flows freely between the tank 9 and more precisely its chamber 15, and the cushion 4 of the inflatable cuff 3. It should be observed that the spring 17 is dimensioned so as to maintain a pressure lying in the range 61 mbar to 70 mbar in the inflatable element 2. This pressure applied by the cuff against the urethra is sufficient to ensure continence but remains insufficient to stop arterial and venous blood flow. The compressed tissue thus remains irrigated.

When the patient desires to urinate, the inflatable element 2 needs to be emptied into the tank 9 so as to eliminate compression on the urethra. For this purpose, the patient actuates the pump 11 by pressing on the deformable wall 35.

Under the action of pressure from the pump 11, the drain valve 49 is closed and the fluid contained in the supply 34 of the pump 11 pushes against the valve 47 that was closing the circuit 41, thereby enabling the chamber 15 of the tank 9 to be filled.

When the pump 11 applies suction:
the circuit 42 opens insofar as the drain valve 49 occupies its open position since the fluid pressure inside the inflatable cushion 4 is greater than the pressure inside the supply 34 of the pump 11. The inflatable element 2 empties into the supply 34 of the pump 11; and
the circuit 41 is closed under the action of the spring of the valve 47 since the pressure inside the pump 11 is less than the pressure in the chamber 15.

Pressure is applied repeatedly to the pump 11 until the inflatable element 2 is empty. The patient knows that the inflatable element 2 is empty when the pump is flat. The patient can then urinate insofar as the inflatable cushion 4 no longer applies pressure. The pump 11 thus enables the fluid coming from the inflatable cushion 4 to be transferred into the chamber 15, which chamber is naturally dimensioned so as to enable the inflatable cushion 4 to be emptied completely.

Simultaneously, the circuit 40 remains permanently open, such that the tank 9, via its chamber 15, fills progressively both the inflatable element 2 and also the supply 34 of the pump 11 via the circuit 42. Filling takes place slowly via the calibrated orifice 45 (over about 180 seconds). The patient has enough time to empty the bladder completely before the cuff 3 once more compresses the urethra as explained above, the chamber 15 being dimensioned to enable the inflatable cushion 4 to be filled so that the cuff occupies its occlusive position. In practice, the chamber 15 possesses a fluid volume that is much greater than the volume of fluid needed for filling the inflatable cushion 4.

The artificial urinary sphincter may be blocked by placing the switch 60 in the deactivated position. This deactivation is necessary for a duration of about 2 months after implantation so as to avoid applying any compression to the urethra that has been traumatized by the surgery.

It can be seen from the above description that, in order to be implanted, the surgical implant 1 requires only a single perineal incision in order to place the inflatable element 2 around the urethra and to slide the control unit 7 into a space in the scrotum. Compared with the prior art, there is no pelvic approach, and all of the risks associated with implanting a pressure-regulator balloon between the bladder and the iliac vessels are avoided so a short hospital stay is possible. This ease of implantation is due to the control unit 7 having the tank 9 and the manual pump 11 incorporated therein. Furthermore, using a leaktight chamber of volume that is variable under the action of an elastically movable piston enables a pressure-regulator system to be provided that is particularly reliable and effective. Furthermore, the surgical implant 1 is practically ready for implantation, it being necessary merely to fill it with physiological serum prior to implantation.

In the above description, the inflatable element 2 is in the form of a cuff 3 suitable for surrounding an organ that has an internal passage, so as to constitute an artificial sphincter. Naturally, it is possible to envisage the inflatable element being in the form of an elongate element suitable for forming a penile implant.

The invention claimed is:

1. A surgical implant comprising:
   an inflatable element (2) that is inflatable in response to fluid pressure;
   a tank (9) for fluid under pressure in communication with the inflatable element to regulate the pressure of said element;
   a manually controlled pump (11) in communication firstly with the inflatable element via a first one-way check valve (49), and secondly with the tank via a second one-way check valve (47); and
   a control unit (7) incorporating the tank (9) and the manual pump (11), the control unit presenting a through opening (12) for the fluid, the opening being in communication firstly on the inside of the control unit (7) with the tank (9) and the manual pump (11), and secondly on the outside of the control unit solely with the inflatable element (2) via a catheter (6) mounted between the inflatable element (2) and the control unit (7);
   wherein the tank (9) defines a leak tight chamber (15) of fluid under pressure, the chamber comprising a movable piston (16) biased by a spring (17);
   wherein the leak tight chamber (15) of fluid under pressure is defined inside a rigid cylinder (18) between a closure end wall (32) of the cylinder and the movable piston (16); and
   wherein the spring (17) is mounted inside the cylinder (18) bearing against a mounting support (19).

2. A surgical implant according to claim 1, characterized in that a sealing membrane (31) is fastened between the piston (16) and the cylinder (18).

3. A surgical implant according to claim 2, characterized in that the cylinder (18) is closed opposite from the piston (16) by an end wall defining:
   a first connection (40) providing communication between the chamber (15) and the through opening (12);
   a second connection (41) providing communication between the chamber (15) and the pump (11); and
   a third connection (42) providing communication between the pump (11) and the through opening (12).

4. A surgical implant according to claim 3, characterized in that:
   the first connection (40) providing communication between the chamber (15) and the through opening (12) is provided with a calibrated leak orifice (45) to regulate the pressure of the inflatable element (2); and
   the second connection (41) providing communication between the pump (11) and the chamber (15) is provided with the second one-way check valve (47) that is elastically biased towards its closed, rest position.

5. A surgical implant according to claim 3, characterized in that it includes a control switch (60) for closing the first connection (40) providing communication between the tank (9) and the inflatable element (2).

6. A surgical implant according to claim 5, characterized in that the control switch (60) is accessible from opposing sides of the control unit (7).

7. A surgical implant according to claim 1, characterized in that the spring (17) is immersed in a confined fluid medium that is different from the fluid under pressure and that forms a compensation volume (29) for compensation relative to the volume of the chamber (15).

8. A surgical implant according to claim 7, characterized in that the piston (16) comprises a side defining the chamber (15) and a side opposite from the chamber (15), the side opposite from the chamber (15) defining a compensation volume (29) that is closed by a deformable wall (28) confining the fluid medium in which the spring is immersed.

9. A surgical implant according to claim 1, characterized in that the pump (11) includes a movable actuation wall (35) mounted on the cylinder (18) and internally defining a variable-volume supply of fluid (34) that is in communication with the second and third connections (42 and 41) providing communication between the pump (11) and the through opening (12), and between the pump (11) and the chamber (15) of the tank (9).

10. A surgical implant according to claim 9, characterized in that the wall movable actuation (35) of the pump extends over substantially an entire height of the cylinder (18), being provided with ridges to assist in actuating it.

11. A surgical implant according to claim 1, characterized in that the inflatable element (2) is in the form of a cuff (3) suitable for surrounding an organ having an internal passage so as to be closed or opened by constriction applied by said inflatable element.

* * * * *